United States Patent [19]
Osterwalder et al.

[11] Patent Number: 6,102,696
[45] Date of Patent: Aug. 15, 2000

[54] APPARATUS FOR CURING RESIN IN DENTISTRY

[76] Inventors: J. Martin Osterwalder, 2119 Via Tiempo, Cardiff, Calif. 92007; Alan Austin Creamer, 16065 Via De Las Palmas, San Diego, Calif. 92091

[21] Appl. No.: 09/302,526

[22] Filed: Apr. 30, 1999

[51] Int. Cl.$^7$ ...................................................... A61C 3/00
[52] U.S. Cl. ............................................. 433/29; 433/229
[58] Field of Search ............................ 433/29, 215, 229; 362/120, 119

[56] References Cited

U.S. PATENT DOCUMENTS

| 5,328,368 | 7/1994 | Lansing et al. | 433/116 |
| 5,634,711 | 6/1997 | Kennedy et al. | 362/119 |

*Primary Examiner*—John J. Wilson
*Assistant Examiner*—Melba Bumgarner
*Attorney, Agent, or Firm*—Frank D. Gilliam

[57] ABSTRACT

A self contained light source for curing light initiated resins used to coat teeth as veneers and fill cavities and chips in teeth in aesthetic or restorative procedures. The source includes an elongated container holding a battery and electronic compartment at one end and a light emitting window at the other. A plurality of closely space light emitters, typically light emitting diodes or laser diodes, are arrayed to direct light to a common focal point. The light is directed out of the container toward a tooth bearing the resin to be cured to a hard, stable state. The light emitters produce light in a region of the spectrum to which the resin curing initiators is sensitive, typically blue light. The light emitters are preferably mounted on concave edged printed circuit so that they are all oriented inwardly toward the focal point. Microlenses may be used with each light emitter to further concentrate light toward the focal point. Preferably, a light transparent barrier sleeve is placed over the light emitting end of the container and replaced between patients.

19 Claims, 1 Drawing Sheet

APPARATUS FOR CURING RESIN IN DENTISTRY

FIELD OF THE INVENTION

This invention relates to the curing of liquid resin coatings applied to teeth to cover tooth surfaces and to fill cavities, chips and the like. The resins harden to produce a tough, hard coatings when subjected to irradiation with light at predetermined wavelengths.

BACKGROUND OF THE INVENTION

Since the development of light-cured resins suitable for use on tooth surfaces, a number of different devices and methods have been developed for curing the resins.

Originally, halogen lamps were used, directing the energy through a narrow steel tube or along a fused glass bundle wave guide to the treatment site. Since the output is broadband, the lamp, tube or waveguide must contain a blue filter to remove most of the unwanted energy outside the desired frequency band. This arrangement is large, inefficient, complex and requires connection to an AC electrical outlet. The filters tend to have short useful lives and pass some other light in addition to the desired blue light, which will tend to undesirably heat the treatment area and the lamp reflectors degrade with time.

Powerful lasers, such as argon ion lasers which emit at a number of discrete spectral lines have been used. These lasers are expensive, have a limited lifetime, are inefficient converters of electrical energy into blue light and generate large amounts of heat. The use of diode pumped crystals which double the input frequency into the blue spectrum have been proposed, as have plasma arc tubes. These units are large, complex and expensive, requiring electrical connection to a high power source. The handpiece used to direct the energy to the treatment site tends to be large and to be restrictive and unwieldy due to the wiring to an external electrical supply.

Attempts have been made to use the recently developed blue light emitting diodes (LED), which require no filter. Typically, a plurality of LED's are arrayed at the large end of a tapered glass member or are positioned so that each LED feeds one fiber of a fiber bundle. Unfortunately, these arrangements have considerable coupling and taper/fiber losses.

Thus, there is a continuing need for improved light sources for use in curing resins coated on teeth which will produce a narrow band of wavelengths, usually in the blue light region, that are simple, reliable, efficient and inexpensive, that are small, light weight and self contained with no need for external wiring.

SUMMARY OF THE INVENTION

The above-noted problems, and others, are overcome by a device for directing light of predetermined frequencies to teeth that have been coated with a light-responsive synthetic resin responsive to the predetermined frequencies that includes an array of very small light emitting sources oriented to direct light to a common focal point. The resins of interest here are referred to as "dental resins". The device is housed in a small, compact, self-contained, elongated container which houses a power source (which may be any self-contained source, such as batteries, a high capacity capacitor, etc.), the required electronic circuitry and the light emitters. Each light emitter may be desirably provided with a miniature focussing element, such as a micro lens.

In a first embodiment of this invention, the light sources may be blue light emitting LED's, emitting in the wavelengths to which the resin initiator is most sensitive, typically in the about 450 to 490 nm range, the range where present camphoroquinone initiated resins are primarily sensitive. Typical LED's have a circular cross section with diameters of about 3 mm. Arrays of LED's are assembled with the LED's closely spaced or in contact. Typically, square cross section arrays, typically 3×3, 4×4, 5×5, etc., may be used, as may be other arrangements such as hexagonal arrays.

The LED's are arranged with all of them oriented to focus at the same point. Small micro lenses may be used over the LED's to improve focus and adjust the focal distance. The array of LED's are preferably housed at the distal end of an elongated container, with the LED array oriented to direct light out the side of the distal end. The proximal end of the container contains a battery, the conventional control circuitry and a suitable on-off switch. Generally, the container will taper from the relatively large diameter battery area to the distal end. A barrier layer, typically plastic film, an elastic material, etc. which is substantially transparent to the blue light covers the distal end and will be changed between patients.

In a preferred arrangement, the rows of LED's are each mounted on a concave edge of a printed circuit board, so that each LED faces toward the desired focal point. The boards are stacked at suitable angles to each other to form adjacent rows and carry any desired microelectronics, such as the usual resister associated with each LED. Any suitable micro lens can be secured to the output end of each LED.

In another embodiment of this invention, each light emitter is a laser diode designed to emit blue light in the desired wavelength spectrum. Typical laser diodes are circular and have diameters of about 5.6 mm. The laser diodes may be arranged in the same manner as the LED's in the embodiment described above. However, because of the coherent light emitted by laser diodes, micro lenses are more efficient in directing light to a precise, distant, focal point. Because of this characteristic, it is preferred that an array of the sort described above can be positioned near the proximal end to an elongated container, with the required battery and required electronics between the proximal container end and the laser diodes.

The laser diodes are oriented to focus at a point within the container near the distal container end, which may be several inches away. A reflecting device at the distal end reflects the light from the laser diodes out the side of the distal end. While a first surface mirror is convenient and simple, if desired any other suitable light reflective means, such as a prism, may be used. The common focal point for all the laser diodes may be slightly short of the mirror or slightly beyond the mirror so that the light from the mirror will spread to a predetermined extent to cover a desired area of a tooth adjacent to the distal end.

Thus, it is an object of this invention to provide a very compact dental resin curing apparatus that has a very small diameter distal end for convenient use in a patient's mouth for curing a resin coating on a tooth. Another object is to provide an entirely self contained dental resin curing apparatus having no external wiring or other connections. A further object is to provide a reliable, long lived, dental resin curing apparatus. Yet another object is to provide a light weight, compact dental resin curing apparatus. Still another object is to provide an efficient dental resin curing apparatus which produces a narrow wavelength band in the region to which dental resins are most sensitive without the need for any filtration.

BRIEF DESCRIPTION OF THE DRAWING

Details of the invention, and of preferred embodiments thereof, will be further understood upon reference to the drawing, wherein.

DETAILED DESCRIPTION OF PREFERRED EMBODIMENTS

Figure 1:
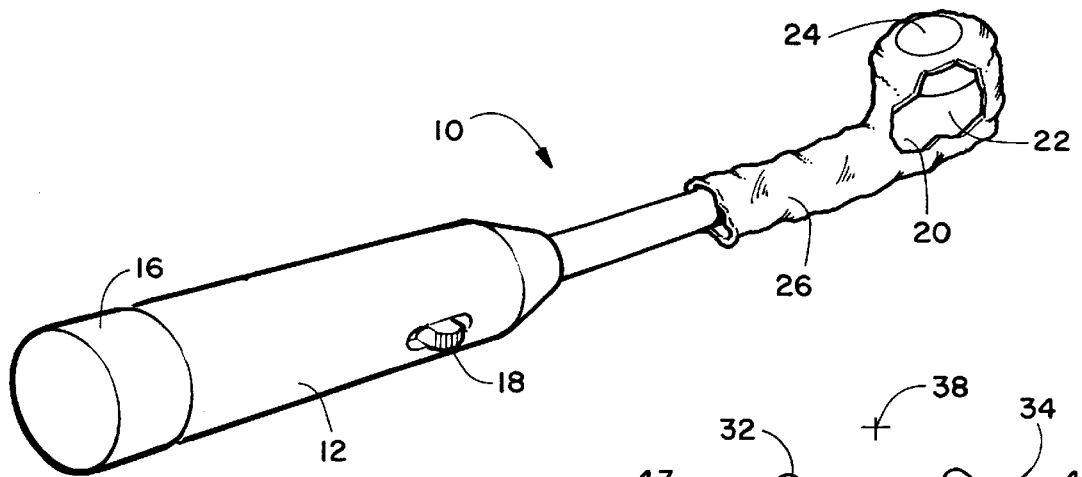
FIG. 1 is a perspective view of a first embodiment of an apparatus for curing resin on a tooth in accordance with this invention.

Referring to FIG. 1 there is seen a perspective view showing the exterior of a first embodiment of the dental resin curing apparatus of this invention.

The apparatus is contained in an elongated container 10, with a proximal portion 12 containing a self contained power source, such as a battery 28, preferably rechargeable via a connection 14 and all necessary electronic components. A removable cap 16 permits removal and replacement of the battery. A conventional, preferably waterproof, push-button switch 18 is provided for turning the unit on and off. Any conventional momentary on switch or the like may be used.

At the distal end 20 of container 10 a housing 22 is provided for holding the light emitters, as detailed below. Housing 22 preferably has a window 24 at the side which is transparent to the light wavelengths generated by the light emitters. While an opening could be used instead of a window, the window is preferred to prevent entry of contaminants into the container. While it is preferred that light from the light emitters exit at approximately 90° to the container centerline for ease of application of the emitted light to various teeth, any other suitable angle may be used as desired. If desired, housing 22 could be made rotatable about one or more axes to permit more convenient application of light to different portions of a tooth.

Figure 2:
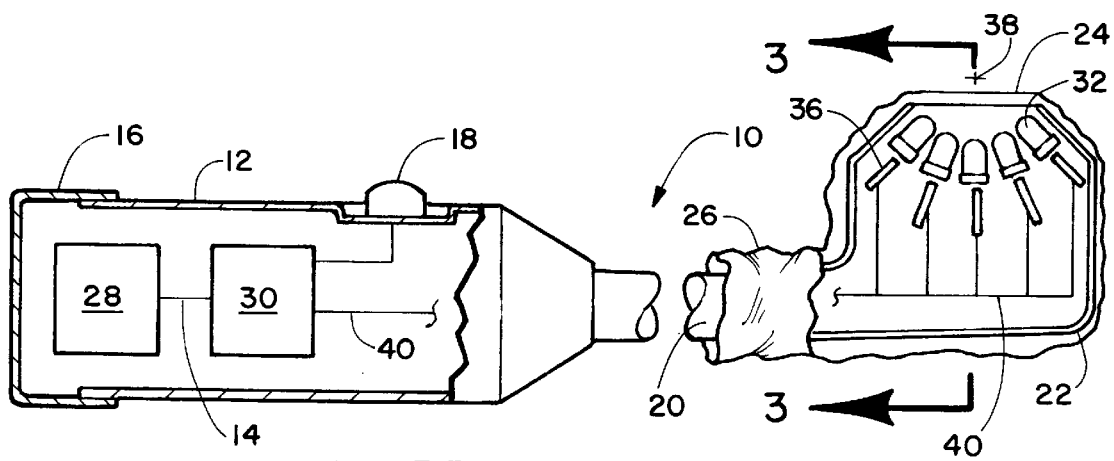
FIG. 2 is a schematic side view of said first embodiment with the near side of the container removed.

Preferably, a easily removable clear plastic barrier sleeve 26 is provided to be slipped over distal end 20 (or the entire unit, as desired) and removed and replaced with a new sleeve between patients to prevent cross-contamination. Sleeve 26 may have any suitable configuration. In a preferred embodiment, sleeve 26 would be an elastic, rubbery, transparent tube that can be stretched over distal end 20 and temporarily held in place by tube elasticity, as shown in FIG. 2. Alternatively, if desired, sleeve 26 could be a flexible, substantially inelastic, tube large enough to fit over housing 22 with an internal tacky end layer at the open end to temporarily bond the sleeve to distal end 20. If desired, sleeve 26 could contain the entire container 10 and be sealed against entry of moisture.

Figure 3:
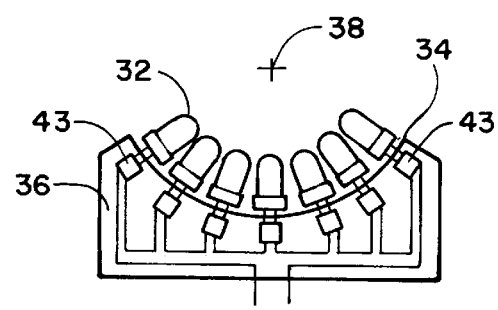
FIG. 3 is a schematic section view taken on line 3—3 in FIG. 2.

FIGS. 2 and 3 show the internal components of the apparatus in schematic representation, with the near side of container 10 removed for clarity. Battery 28 is located at the extreme proximal end 12 for easy replacement by removing cap 16. Any other suitable means for providing access to battery 28 may be provided, as desired. Adjacent to battery 28 a housing 30 is provided for any necessary electronic components necessary to operate the light emitters.

Rows of individual light emitters 32 are mounted on a concave edge 34 of circuit boards 36, as best seen in FIG. 3.

The radius of curvature of concave edge 34 (which is preferably circular) is selected so that light from all emitters 32 is focussed at substantially the same focal point, as schematically indicated at 38. Thus, a dentist can move the apparatus to have the focal point at the resin surface to apply maximum energy where a very small area is to be cured or could move the emitter window 24 slightly further away to spread the light energy over a larger area of slightly less intense light, as desired.

For improved performance, the inclusion of a microlens over the output surface of each light emitter is preferred to collimate and condense the light toward the desired focal point.

Each circuit board 36 has surface wiring that connects to interconnect wires 40 and then to diode laser 42 to the electronic components in housing 30. The surface wiring on the circuit board can include the conventional small resistor 43 for each light emitter. In the preferred embodiment, all of the light emitters 32 will be on at the same time for maximum light intensity and most rapid resin curing, although rows of light emitters 32 could, if desired, be separately switched to permit variation in total emitted light intensity. In the embodiment shown in FIGS. 2 and 3, light emitters 32 are illustrated as LED's incorporating micro lenses for focusing and concentrating light, although other light emitters may be used, as discussed below.

Figure 4:
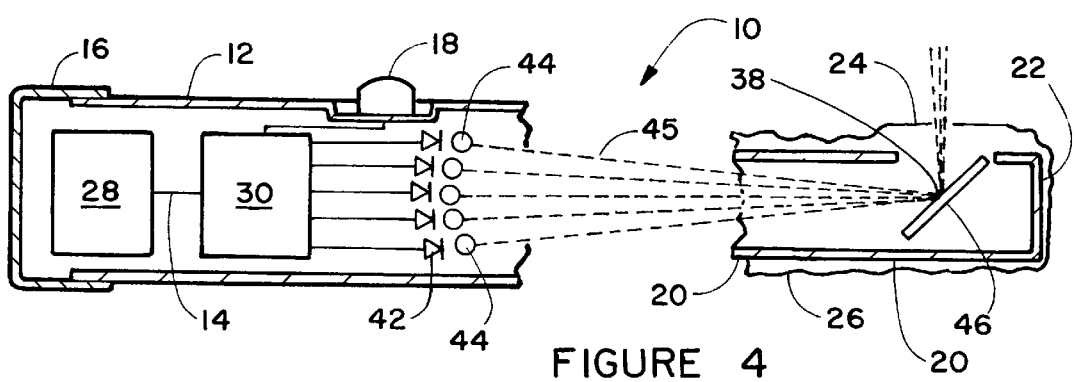
FIG. 4 is a schematic side view of said second embodiment with the near side of the container removed.

A second embodiment of the apparatus of this invention is schematically shown in FIG. 4. As before, the apparatus includes an elongated container 10 having a wider, generally cylindrical, proximal portion 12 for housing a battery 28, a housing 30 for any necessary electronics and a narrower, tapered, distal end 20 having a housing 22 at the distal end from which the light is emitted.

In this embodiment, the light emitters are illustrated as diode lasers 42 with adjacent micro lenses 44 for concentrating light toward the focal point. Both of the diode laser 42 and microlens 44 arrays will be in rows, as discussed above, arranged with concave, preferably spherical, orientation to point toward a focal point 38. Light paths for light from the shown diode lasers are schematically illustrated by dashed lines 45. While the light paths are shown passing along the distal portion in air, if desired, this portion could be any suitable medium transparent to the light being transmitted, such as glass or plastic. The radius of the concave orientation is the distance between each row of diode lasers 42 or microlenses 44 and focal point 38. A first surface mirror 46 is provided in distal end housing 22 to direct the combined emitted light out through window 24 at a predetermined angle, preferably about 90° to the unit centerline. If desired, a larger window could be provided and mirror 46 could be pivotable to change the angle at which the light passes through window 24.

The distance between mirror 46 and focal point 38 will be selected so as to provide a "bundle" of emitted light rays covering a desired area on a tooth. If desired, mirror 46 could be movable toward or away from focal point 38 to change the diameter of the emitted light ray bundle.

Preferably, replaceable barrier sleeves 26 are provided for replacement between patients. The flexible sleeves described above may be used or, in the case where the distal end is cylindrical or uniformly tapered, a rigid transparent sleeve with one closed end could be slipped over the distal end and releasably held in place by a detent, threads, or the like.

Any suitable light emitters 32 may be used in either embodiment. For best results, either blue light emitting LED's as shown in the embodiment of FIGS. 2 and 3 or blue light producing diode lasers as shown in the embodiment of FIG. 4. Typical blue light LED's include Model NSPB300A LED's from Nichia. Typical blue light emitting diode lasers include Model NJHV500 from Nichia.

For the embodiment of FIG. 4, diode lasers are optimum, since the emitted light is coherent and can be well collimated, so that little light is lost between the diode laser and the tooth being treated. While LED's can be used in the FIG. 4 arrangement, there will be considerably greater light losses. By positioning the light emitter array at a wide region in container 10, a relatively large array may be used. Where LED's are to be used, the embodiment of FIGS. 2 and 3 is optimum, since positioning the emitters near the focal point will limit light loss. Diode lasers can, of course, be used as the emitters in the FIGS. 2 and 3 embodiment.

If desired, in the embodiment of FIG. 4, the light rays 45 may pass through conventional individual optical fibers, or the light rays could pass through a bundle of optical fibers having a wide end adjacent to microlenses 44, or to diode lasers 42 if microlenses 44 are not used. Light leaving the ends of the fiber optics can be reflected by mirror 46. Alternatively, the optical fibers may be bent approximately 90° at the location shown in FIG. 4 for mirror 46 so that light leaving the fiber objects will have the path shown. In this embodiment, mirror 46 would not be required.

The apparatus of this invention may be used to cure any suitable dental resin. A typical dental resin comprises a 1:1 mixture, by weight, of bis-phenol-2bis(2-hydroxypropyl) methacrylate and tri(ethylene glycol)dimethacrylate monomers. The mixture further includes a camphoroquinone photoinitiator and a tertiary amine reducing agent. Fillers such as silica particles, and colorants are generally included to give the desired hardness level and color.

While certain specific relationships, materials and other parameters have been detailed in the above description of preferred embodiments, those can be varied, where suitable, with similar results. Other applications, variation and ramifications of the present invention will occur to those skilled in the art upon reading the present disclosure. Those are intended to be included within the scope of this invention as defined in the appended claims.

I claim:

1. A self contained light source for curing a synthetic resin coating on teeth, which comprises:

an elongated container having a central longitudinal axis and having proximal and distal portions lying along said longitudinal axis;

an array of closely spaced light emitting means within said container;

mounting means for orienting said light emitting means to emit light toward a common focal point;

said light emitting means comprising an array of light emitting diodes, each light emitting diode for emitting light in the blue region of the light spectrum, each light emitting diode having a microlens for directing emitted light toward said common focal point;

means for directing said light out of said elongated container from said distal portion thereof in a predetermined pattern;

self contained electrical power means within said proximal portion of said elongated container for powering said emitter means.

2. The self contained light source according to claim 1 wherein said means for directing light out of said container comprises a window transparent to said emitted light in a wall of said distal portion and wherein said light emitting diodes are mounted in said distal portion adjacent to said window and said common focal point is outside said container.

3. The self contained light source according to claim 1 wherein said mounting means comprises at least one printed circuit board having a concave edge and means for mounting a plurality of said light emitting diodes along said concave edge with said light emitting diodes oriented toward said common focal point.

4. The self contained light source according to claim 1 wherein said array of light emitting means comprises a plurality of diode lasers, each for emitting light in the blue region of the light spectrum.

5. The self contained light source according to claim 4 wherein:

said plurality of diode lasers is mounted in said proximal portion;

said common focal point is within said distal portion and lies approximately on said longitudinal axis;

said means for directing light out of said container comprises a window transparent to said emitted light in a wall of said distal portion;

said window means being away from said longitudinal axis;

further including mirror means for reflecting said light through said window.

6. The self contained light source according to claim 4 wherein said mounting means aligns said diode lasers in a first spherical pattern, the radius of which is the distance between said diode lasers and said common focal point.

7. The self contained light source according to claim 6 wherein each of said laser microlenses lying oriented in a second spherical pattern, the radius of which is the distance between said microlenses and said common focal point.

8. The self contained light source according to claim 1 further including a removable barrier sleeve formed from a material substantially transparent to said light and positioned over said distal portion.

9. The self contained light source according to claim 1 wherein said self contained electrical power means is a rechargeable battery.

10. A self contained light source for curing a synthetic resin coating on teeth, which comprises:

an elongated container having a central longitudinal axis and having proximal and distal portions lying along said longitudinal axis;

a plurality of printed circuit boards mounted adjacent each other in said distal portion;

each of said printed circuit boards having a concave edge;

a plurality of closely spaced light emitting diodes mounted on said concave edge;

said printed circuit boards oriented so that said light emitting diodes emit light toward a common focal point outside said container;

said light emitting diodes being capable of emitting said light in a predetermined frequency range that initiates curing of a predetermined synthetic resin; and battery means within said proximal portion of said elongated container for powering said emitter means.

11. The self contained light source according to claim 10 further including a microlens positioned adjacent to each light emitting diode to receive light emitted therefrom and concentrate said light toward said common focal point.

12. The self contained light source according to claim 10 further including a removable barrier sleeve formed from a material substantially transparent to said light and positioned over said distal portion.

13. The self contained light source according to claim 10 further including window means positioned to allow said light to egress said container to said common focal point.

14. A self contained light source for curing a synthetic resin coating on teeth, which comprises:

an elongated container having a central longitudinal axis and having proximal and distal portions lying along said longitudinal axis;

an array of closely spaced diode lasers within said proximal portion;

said diode lasers oriented to emit light toward a common focal point lying approximately on said longitudinal axis within said distal portion;

each of said diode lasers aligned in a first spherical surface pattern, the radius of which is the distance between said diode lasers and said common focal point said diode lasers emitting said light in a predetermined frequency range that initiates curing of a predetermined synthetic resin;

means for directing said light out of said container; and self contained electrical means within said proximal portion of said elongated container for powering said emitter means.

15. The self contained light source according to claim 14 further including a microlens positioned adjacent to each diode laser to receive light emitted therefrom and concentrate said light toward said common focal point.

16. The self contained light source according to claim 14 further including a removable barrier sleeve formed from a material substantially transparent to said light and positioned over said distal portion.

17. The self contained light source according to claim 14 wherein said means for directing said light out of said container comprises window means transparent to said light and positioned in a wall of said distal portion, off of said longitudinal axis and mirror means for reflecting said light from said longitudinal axis through said window.

18. The self contained light source according to claim 14 wherein said self contained electrical power means is a rechargeable battery.

19. A self contained light source for curing a synthetic resin coating on teeth, which comprises:

an elongated container having a central longitudinal axis and having proximal and distal portions lying along said longitudinal axis;

an array of closely spaced light emitting means within said container;

mounting means for orienting said light emitting means to emit light toward a common focal point;

said light emitting means comprising a plurality of diode lasers, each for emitting light in the blue region of the light spectrum said plurality of diode lasers is mounted in said proximal portion; said common focal point is within said distal portion and lies approximately on said longitudinal axis;

means for directing said light in the elongated container from said distal portion comprising a window off said longitudinal axis and mirror means for reflecting said light through said window; and self contained electrical power means within said proximal portion of said elongated container for powering said emitter means.

* * * * *

UNITED STATES PATENT AND TRADEMARK OFFICE
Certificate

Patent No. 6,102,696                                                        Patented: August 15, 2000

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: J. Martin Osterwalder, Cardiff, CA.

Signed and Sealed this Sixth Day of July 2004.

NICHOLAS D. LUCCHESI
*Supervisory Patent Examiner*
Art Unit 3732